United States Patent [19]
Smith et al.

[11] Patent Number: 5,069,204
[45] Date of Patent: Dec. 3, 1991

[54] INHALER

[75] Inventors: David K. Smith, Loughborough; Anthony C. L. Wass, Stamford, both of United Kingdom

[73] Assignee: Riker Laboratories, Inc., St. Paul, Minn.

[21] Appl. No.: 569,071

[22] Filed: Aug. 17, 1990

[30] Foreign Application Priority Data

Aug. 23, 1989 [GB] United Kingdom ............... 8919131

[51] Int. Cl.$^5$ ............................................. A61M 11/00
[52] U.S. Cl. ........................... 128/200.23; 128/203.12; 128/203.15
[58] Field of Search ............ 128/200.23, 200.14, 128/200.17, 203.12, 203.15

[56] References Cited

U.S. PATENT DOCUMENTS

| 3,187,748 | 6/1965 | Mitchell et al. | 128/173 |
|---|---|---|---|
| 3,456,644 | 7/1969 | Thiel | 128/173 |
| 3,456,646 | 7/1969 | Phillips et al. | 128/173 |
| 3,506,004 | 4/1970 | Mann et al. | 128/200.23 |
| 3,565,070 | 2/1971 | Hanson et al. | 128/173 |
| 3,598,294 | 8/1971 | Hedrick et al. | 222/402 |
| 3,605,738 | 9/1971 | Ciranna | 128/173 |
| 3,635,219 | 1/1972 | Altounyan et al. | 128/203.15 |
| 3,636,949 | 1/1972 | Kropp | 128/173 |
| 3,645,645 | 2/1972 | Gammill et al. | 415/163 |
| 3,732,864 | 5/1973 | Thompson et al. | 128/173 |
| 3,739,950 | 6/1973 | Gorman | 128/200.23 |
| 3,789,843 | 2/1974 | Armstrong et al. | 128/173 |
| 3,814,297 | 6/1974 | Warren | 222/402 |
| 3,826,413 | 7/1974 | Warren | 128/200.23 |
| 3,865,279 | 2/1975 | James | 128/200.23 |
| 4,130,116 | 12/1978 | Cavazza | 128/200.23 |
| 4,414,972 | 11/1983 | Young et al. | 128/200.23 |
| 4,664,107 | 5/1987 | Wass | 128/200.23 |
| 4,678,106 | 7/1987 | Newell et al. | 222/162 |
| 4,834,083 | 5/1989 | Byram et al. | 128/200.23 |
| 4,934,358 | 6/1990 | Nilsson et al. | 128/200.23 |
| 4,940,051 | 7/1990 | Lankinen | 128/200.23 |

FOREIGN PATENT DOCUMENTS

| 0147028 | 5/1988 | European Pat. Off. |  |
|---|---|---|---|
| 3040641 | 5/1982 | Fed. Rep. of Germany . |  |
| 1269554 | 4/1972 | United Kingdom . |  |
| 1335378 | 10/1973 | United Kingdom . |  |
| 1392192 | 4/1975 | United Kingdom . |  |
| 2061116 | 8/1979 | United Kingdom . |  |
| 2195544 | 4/1988 | United Kingdom | 128/203.12 |
| 2204799 | 11/1988 | United Kingdom | 128/200.14 |

Primary Examiner—Edgar S. Burr
Assistant Examiner—Stephen R. Funk
Attorney, Agent, or Firm—Gary L. Griswold; Walter N. Kirn; Douglas E. Reedich

[57] ABSTRACT

An inhalation device comprising:
(i) a breath-actuated inhaler comprising a medicament reservoir mounted within a housing which comprises a mouthpiece and breath-actuation means which prevents dispensing from the reservoir until a patient inhales through the mouthpiece, and,
(ii) a protective casing surrounding the breath actuated inhaler, the casing comprising a body portion and a movable cover which may be displaced to allow a patient access to the mouthpiece to use the breath-actuated inhaler while it is within the casing, the breath-actuated inhaler being removable from the protective casing and operable outside the casing.

5 Claims, 9 Drawing Sheets

INHALER

FIELD OF THE INVENTION

This invention relates to inhalation activatable dispensers for use with inhalers such as dry powder dispersers and aerosol container assemblies which contain medicaments for inhalation therapy, are pressurized with liquid propellants, and include a metering valve through which a series of metered medicament doses can be dispensed. In particular the invention relates to inhalation activatable dispensers which are removably retained within an outer casing.

BACKGROUND TO THE INVENITON

Inhalation activatable dispensers for use with aerosol container assemblies of the type described above are known, their general purpose being to afford proper coordination of the dispensing of a dose of medicament with the inhalatin of the patient thereby allowing the maximum proportion of the dose of medicament to be drawn into the patient's bronchial passages. Examples of such dispensers are described in British Patent Specification Nos. 1,269,554, 1,335,378, 1,392,192 and 2,061,116 and U.S. Pat. Nos. 3,456,644, 3,645,645, 3,456,646, 3,565,070, 3,598,294, 3,814,297, 3,605,738, 3,732,864, 3,636,949, 3,789,843 and 3,187,748 and German Patent No. 3,040,641.

European Patent No. 147028 discloses an inhalation activatable dispenser for use with an aerosol container in which a latch mechanism releasing vane is pivotally mounted in an air passage between an aerosol outlet valve and a mouthpiece, which latch mechanism cannot be released if force to activate the dispenser is not applied before a patient inhales.

The dispenser generally comprises a housing having a mouthpiece and an air passage therethrough terminating at the mouthpiece, the housing being adapted to receive an aerosol container having a support block with a socket adapted to receive the stem of the valve of the aerosol container and a through orifice communicating between the socket and the air passage, and latch means having parts movable between an engaged position in which movement of the container and the support block toward each other upon the application of a force to bias the container and the support block toward each other is prevented and a release position in which movement of the container and the support block toward each other in response to said force is permitted causing the stem to move to its inner discharge position, the latch means comprising a vane mounted on the housing in the air passageway between the orifice and the mouthpiece for movement toward the mouthpiece under the influence of inhalation through the mouthpiece to release the latch means in which the vane moves toward the mouthpiece from a blocking to a nonblocking position with respect to the passageway in response to inhaling at the mouthpiece and releases the latch means only during the application of said force to bias the container and support block toward each other.

This inhalation device has been received favourably by patients and doctors since it not only overcomes the hand-lung coordination problem but it does so at a very low triggering flow rate (approximately 30 liters/minute) essentially silently, and with a very compact design barely larger than a standard inhaler.

It is an object of the present invention to provide an inhalation activable dispenser within an outer casing.

BRIEF SUMMARY OF THE INVENTION

Therefore according to the present invention there is provided:

(i) a breath-actuated inhaler comprising a medicament reservoir mounted within a housing which comprises a mouthpiece and breath-actuation means which prevents dispensing from the reservoir until a patient inhales through the mouthpiece, and, (ii) a protective casing surrounding the breath actuated inhaler, the casing comprising a body portion and a movable cover which may be displaced to allow a patient access to the mouthpiece to use the breath-actuated inhaler whilst it is within the casing, the breath-actuated inhaler being removable from the protective casing and operable outside the casing.

The arrangement of a removable breath-actuated inhaler within a protective casing has several advantages. The casing surrounds and preferably completely envelopes the inhaler preventing ingress of dust, water and other foreign bodies allowing the inhalation device to be readily carried in a pocket, handbag etc. The inhaler may be used without removing it from the casing by displacing the cover to allow patient access to the mouthpiece. The casing also protects the inhaler, particularly the breath-actuated mechanism, from direct damage and if the casing is damaged the inhaler will probably still function from within the casing. However, if the casing is subjected to severe damage the inhaler may be removed and used in its breath-actuated mode outside the casing. In a preferred embodiment the breath-actuated inhaler comprises means to disable the breath-actuated mechanism thereby allowing the inhaler to be used in a simple press-and-breathe mode which allows test firing.

DESCRIPTION OF PREFERRED EMBODIMENTS

The inhaler preferably comprises an aerosol vial containing a mixture of propellant and medicament and equipped with a metering valve. However, the inhalation device of the invention may comprise a dry powder dispensing device in which the medicament is entrained in the air stream established by the patient's inspiratory effort. Examples of such devices are disclosed in our co-pending British Patent Application No. 8909891.7.

Suitable breath-actuated mechanisms for use in the inhaler are known and are described, for example, in European Patent No. 147028. The breath-actuated mechanism requires a priming or cocking force which moves the aerosol container relative to the valve stem for dispensing when the breath-actuated mechanism has been actuated. In one arrangement of the invention the priming force may be provided by a cocking lever mounted through the protective casing or may be provided by a screw arrangement or when the cover is displaced e.g. by a sliding, lever, geared or cam action or a combination thereof. Alternatively, access to a cocking lever may be gained when the cover is displaced. The priming force may be applied directly to the aerosol container or to the valve e.g. via a nozzle block assembly. The priming force is preferably applied by the cover which may be pivotally mounted to displace upwardly or downwardly to provide access to the mouthpiece. Generally the priming force applied by the cocking lever, cover etc., results in compression of a spring which moves the aerosol container relative to the valve when the breath-actuated mechanism is triggered. When the inhaler is removed from the casing the priming force may be applied manually by squeezing the aerosol container and housing between thumb and finger in a similar manner to a conventional press-and-breathe inhaler.

Alternatively, the inhaler may possess its own cocking lever to apply the primary force when the inhaler is removed from the casing. When the inhaler is within the casing the cocking lever may be uncovered for use when the cover is displaced or may interact with the cover to prime the inhaler during displacement of the cover.

The inhaler is preferably capable of accommodating aerosol vials of different lengths to avoid the necessity of producing completely different devices for each size of vial. Different length vials may be accommodated by forming the body portion of the casing in two or more parts, one part being in the form of a sleeve or shroud which envelops the base and at least part of the body of the aerosol vial. A series of such sleeves may be fabricated to correspond to different lengths of aerosol vials. Alternatively, the body portion of the casing may have an aperture through which the aerosol vial extends thereby obviating the need for producing a range of different size components.

The inhaler preferably incorporates means to provide an indication of the number of doses dispensed and/or remaining in the aerosol container. The indication is preferably visual and the housing of the inhaler and optionally the protective casing may have a transparent window or aperture for viewing.

The invention will now be described with reference to the accompanying drawings in which:

FIG. 1 represents a vertical cross-section through a breath-actuated inhaler suitable for use in the invention, FIG. 2 represents a vertical cross-section through the breath-actuated inhaler of FIG. 1 during operation, FIG. 3 represents a vertical cross-section through the breath-actuated inhaler of FIG. 1 in the press-and-breathe mode, FIG. 4 represents a vertical cross-section through an inhalation device in accordance with the invention which comprises the breath-actuated inhaler of FIG. 1 within a protective casing, FIG. 5 represents a vertical cross-section through the inhalation device of FIG. 4 showing the cover displaced, FIGS. 6*a* and 6*b* represent a perspective view and a cross-section through an alternative inhalation device in accordance with the invention, FIGS. 7*a* and 7*b* represent a perspective view and vertical cross-section through a further inhalation device in accordance with the invention, FIGS. 8*a* and 8*b* represent a vertical cross-section through the upper portion of a further inhalation device in accordance with the invention, FIGS. 9*a* and 9*b* represent a vertical cross-section through an upper portion of a further inhalation device in accordance with the invention, and FIGS. 10*a* and 10*b* represent a vertical cross-section through an upper portion of a further inhalation device in accordance with the invention.

Referring to FIGS. 1 to 5, the breath-actuated inhaler comprises a housing (2) incorporating a mouthpiece (4) and contains an aerosol vial (6). The aerosol vial (6) may be of any suitable size and has a metering valve (not shown) possessing a hollow valve stem (8). The valve stem (8) is held within a nozzle block (10) which has a passage (12) in communication with the mouthpiece (4). Discharge of the metering valve is effected by relative movement between the valve stem (8) and the aerosol vial (6).

The breath-actuation mechanism comprises a vane (14) which is pivotally mounted within the mouthpiece (4), a rocker element (15) which supports a catch (16) pivotally mounted on the rocker at (18). When the breath-actuated mechanism is in its blocking position as shown in FIG. 1 and a cocking force is applied in the direction of the arrows A, movement of the aerosol vial (6) relative to the valve stem (8) is prevented. Such movement is blocked by the rocker element (15), which is prevented from pivotal movement by the catch (16) having a curved surface (17) engaging the curved surface (20) of the vane (14). Thus, when the inhaler is in its breath-actuated mode it is not possible to dispense from the aerosol vial before inhalation through the mouthpiece (4).

When a patient inhales through the mouthpiece as shown in FIG. 2, inhalation causes pivotal movement of the vane. The curved surface (20) of the vane (14) and the curved surface (17) of the catch (16) effectively act as co-operating roller surfaces. Pivotal movement of the vane causes the curved surface (20) to rotate in one direction resulting in curved surface (17) of the catch rotating in the opposite direction. This displacement of the catch moves from a blocking to an unblocking position allowing pivotal movement of the rocker element (15) which in turn allows movement of the vial (6) relative to the valve stem (8) under the influence of the cocking pressure causing the valve to fire.

The inhaler also comprises a switch (22) which may convert the inhaler between a breath-actuated mode and a press-and-breathe mode as may be required for test firing. The switch (22) is pivotally mounted within the housing (2) and comprises a finger (24) which is capable of engaging the catch (16). When the switch (22) is in the breath-actuated mode as shown in FIGS. 1 and 2 there is no engagement between the finger (24) and the catch (16). However, when the switch (22) is pivoted to the press-and-breathe mode as shown in FIG. 3, the finger (24) engages the catch (16), pivoting the catch (16) away from the vane (14) to its unblocking position thereby allowing free movement of the aerosol vial (6) relative to the valve stem (8). In the press-and-breathe mode the valve may be fired at any time. During use the patient will be required to coordinate the cocking force and breathing in order to attain an effective dose. The vane (14) will simply pivot to the roof of the mouthpiece during inhalation.

The breath-actuated inhaler additionally comprises means to provide an indication of the number of doses dispensed and/or an indication of the number of doses remaining. The indicator means comprises a ring (26) mounted for rotation about the aerosol vial, the ring having a plurality of circumferential teeth (28) which co-operate with a plurality of tines (30) mounted on the housing. During the reciprocatory motion of the aerosol vial when the valve is operated one or more of the tines (30) abuts a cam surface on one or more of the teeth (28) causing rotation of the ring (26) by a small increment. Suitable indication markings are present on the side of the ring (26) which may be viewed through a transparent window (32) in the housing to provide the patient with an indication of the contents remaining.

Examples of such means for providing an indication of the contents of an inhaler are disclosed in our co-pending British Patent Application No. 8913893.7, dated 16th June, 1989.

Figure 1:
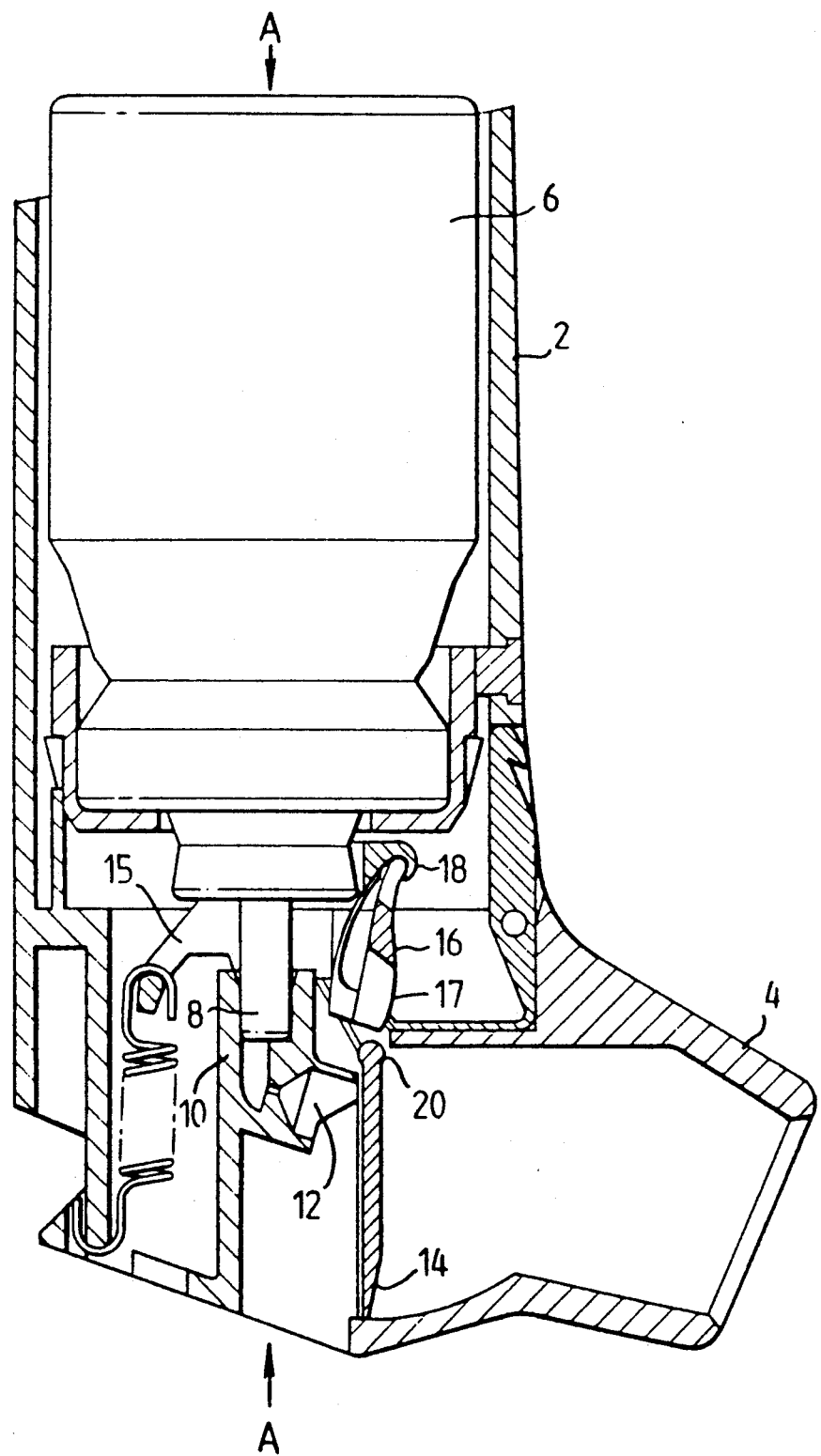
Figure 2:
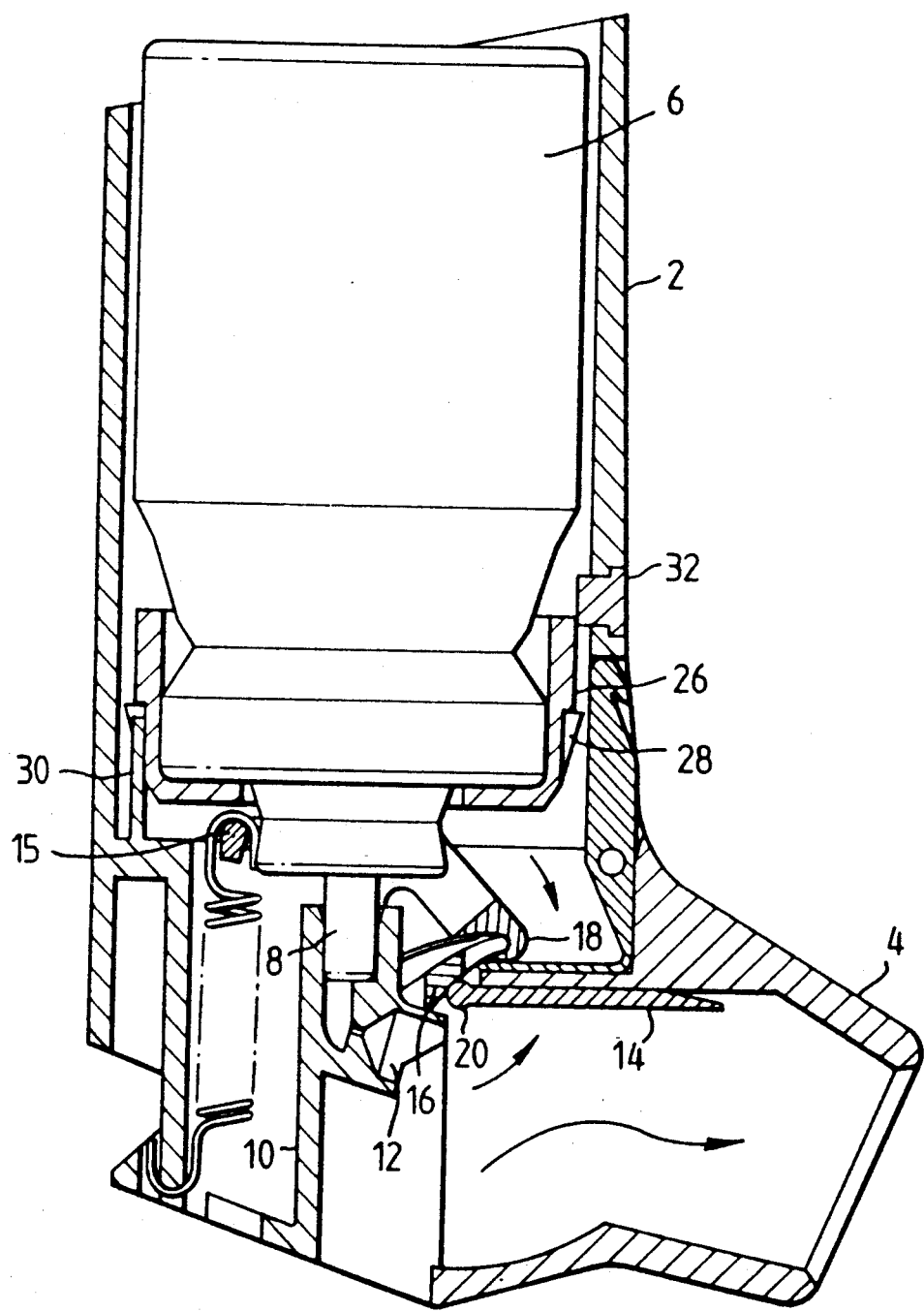
Figure 3:
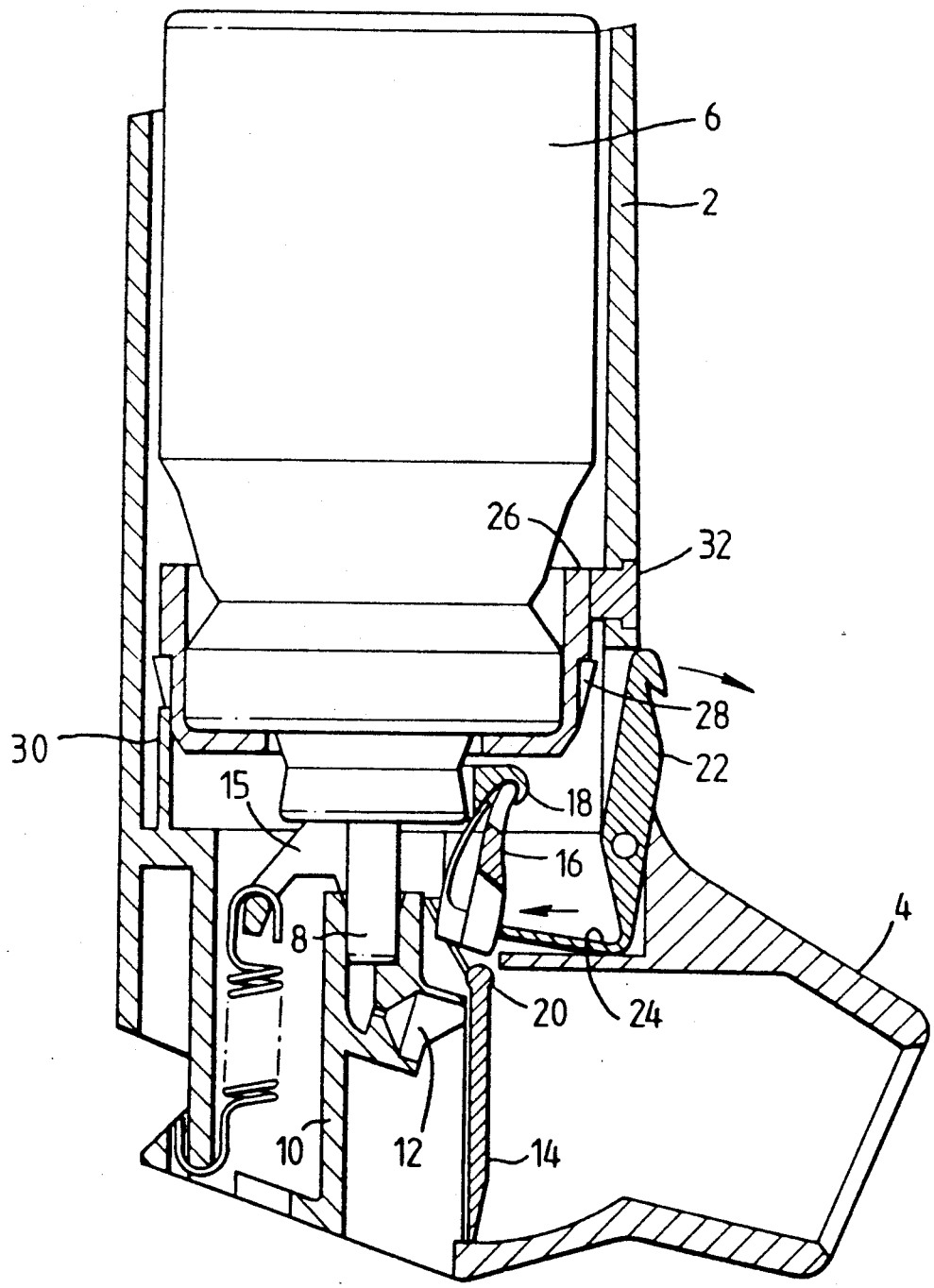
Figure 4:
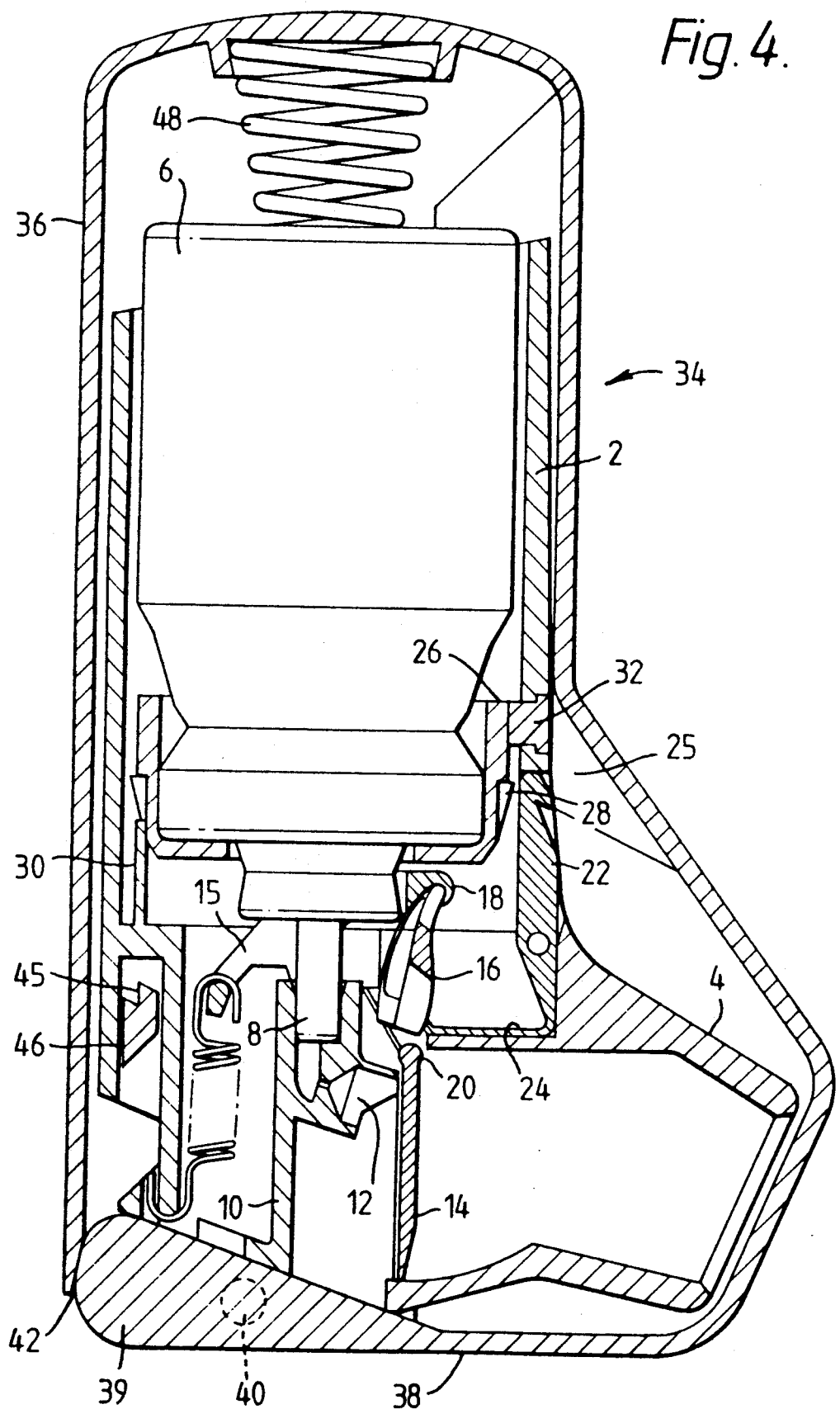
Figure 5:
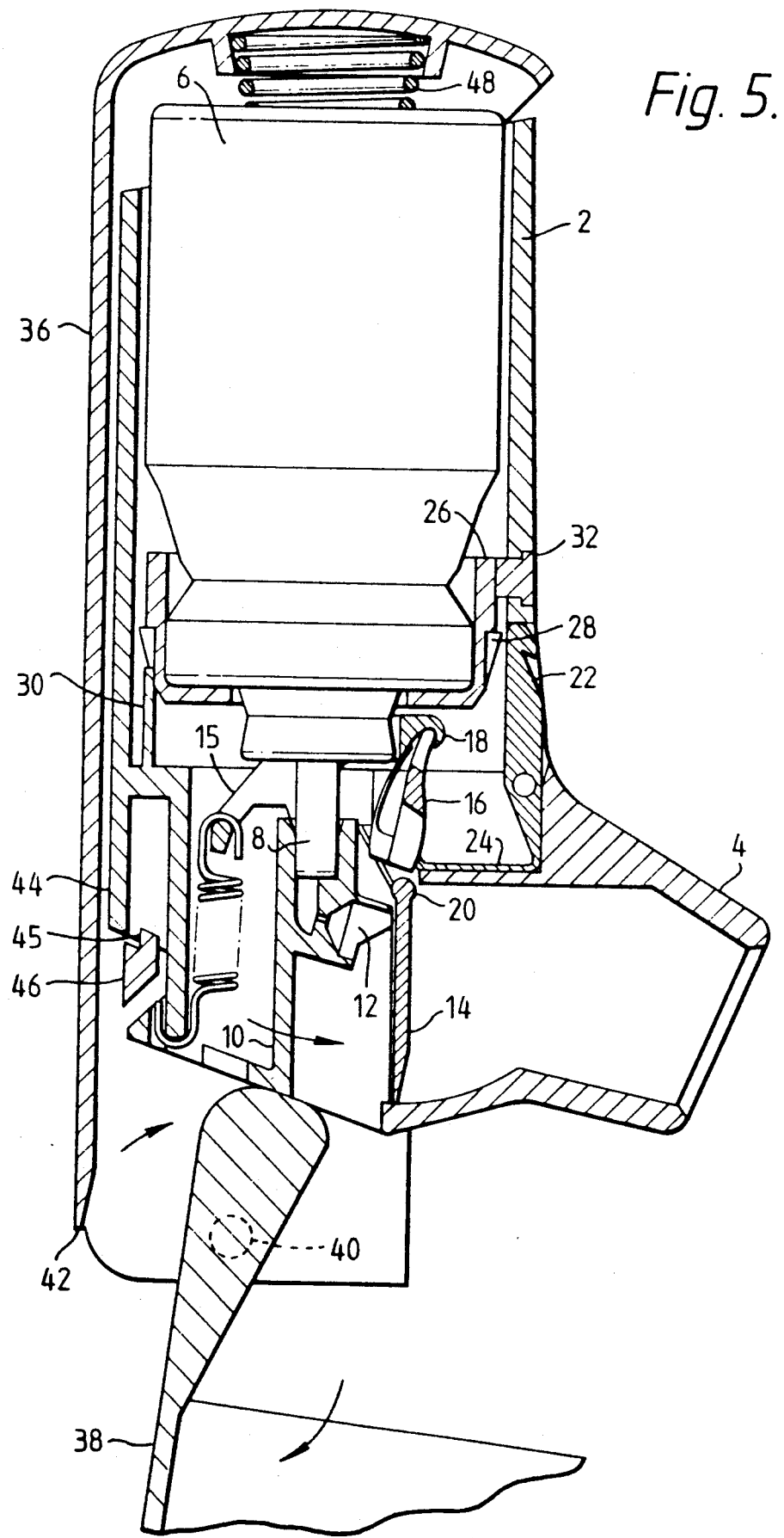

FIGS. 4 and 5 of the accompanying drawings illustrate the breath-actuated inhaler of FIGS. 1 to 3 positioned within a protective casing generally shown at (34). The casing comprises a body portion (36) and a movable cover (38). The protective casing completely envelopes the inhaler preventing ingress of dust and other contaminates and provides robust protection against percussion damage should the inhalation device be dropped etc.

In the embodiment shown in FIGS. 4 and 5 the movable cover (38) is pivoted about pivot point (40) and has a forward protecting extension (39) which when closed fills the gap between pivot (40) and the casing. As the cover is pivoted, this extension (39) acts as a cam (42) on the bar of the inhaler and lifts it up against spring (48). After 90° of movement flange (44) is lifted above first step (45) on projection (46) on the protective cover and is retained on second step, where it remains during remainder of cover movement. On closing, the cover disengages flange (44) from step (45) and allows it to return to original position. Thus, a patient may simply open the cover of the casing and inhale through the mouthpiece to receive a dose of medicament.

The breath-actuated inhaler is retained within the protective cover by a flange (44) on the housing engaging projection (46) on the interior of the protective cover. The inhaler may simply be removed by pushing the inhaler upwards against the cocking spring (48) until the flange (44) and projection (46) disengage and then the inhaler may be readily pulled from the protective casing.

The breath-actuated inhaler may be inserted within the protective cover by fully opening the cover, pushing the top of the inhaler up against the cocking spring and inserting the base until the flange (44) engages the projection (46). When the cover is closed the breath-actuated inhaler will automatically be converted to the breath-actuated mode, even if it is in the press-and-breathe mode, by flange (25) on the cover pushing switch (22) to the breath-actuated position.

Figure 6A:
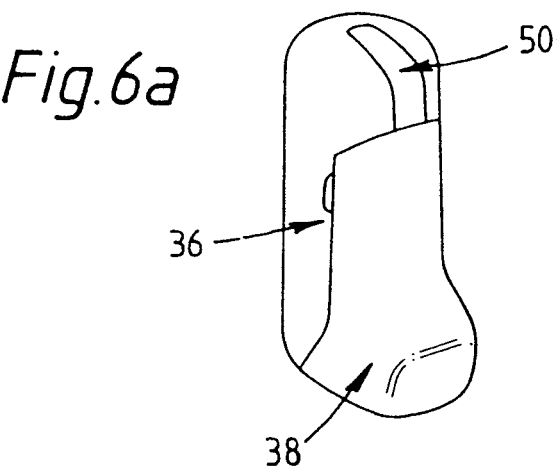
Figure 6B:
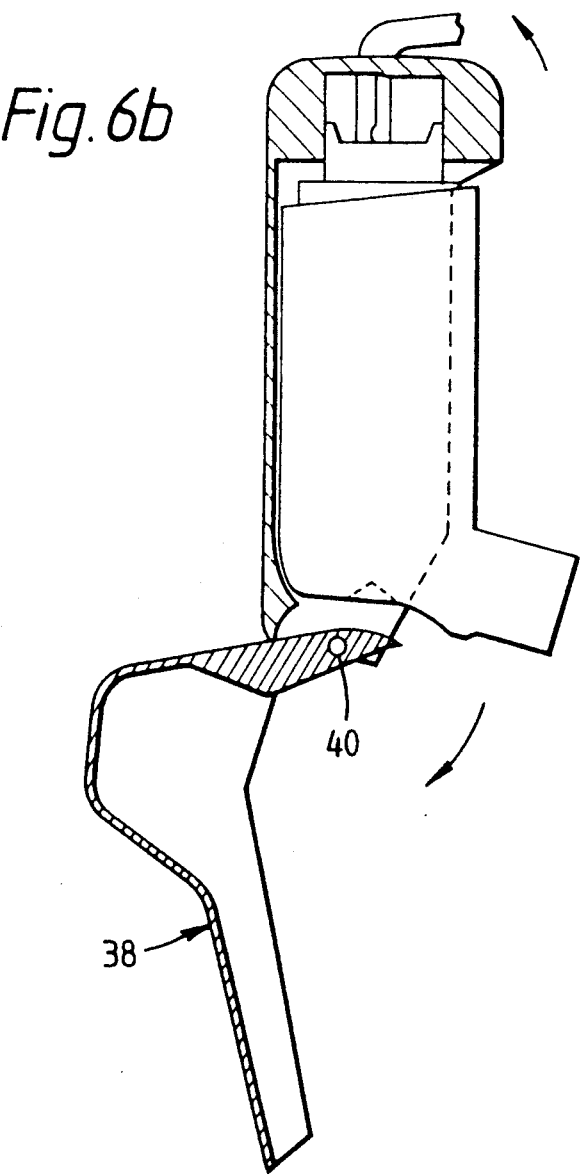

It will be readily appreciated that the protective casing may be constructed in a number of different configurations and it is not necessary for the opening of the cover to automatically apply a cocking force to the inhaler. The arrangement of FIG. 6a and 6b comprises a body portion (36) and a cover (38) which is pivotally mounted about pivot point (40). Opening of the cover (38) does not apply a cocking force to the breath-actuated inhaler. Cocking lever (50) is provided at the top of the protective cover and is constructed and arranged such that upon pivoting the cocking lever (50) downward pressure is applied to the aerosol vial of the breath-actuated inhaler (FIG. 6b).

Figure 7A:
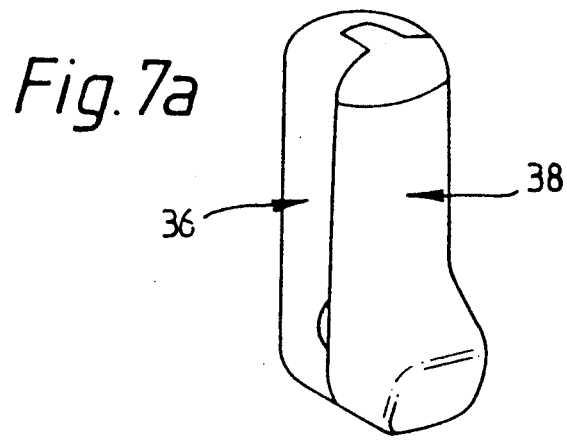
Figure 7B:
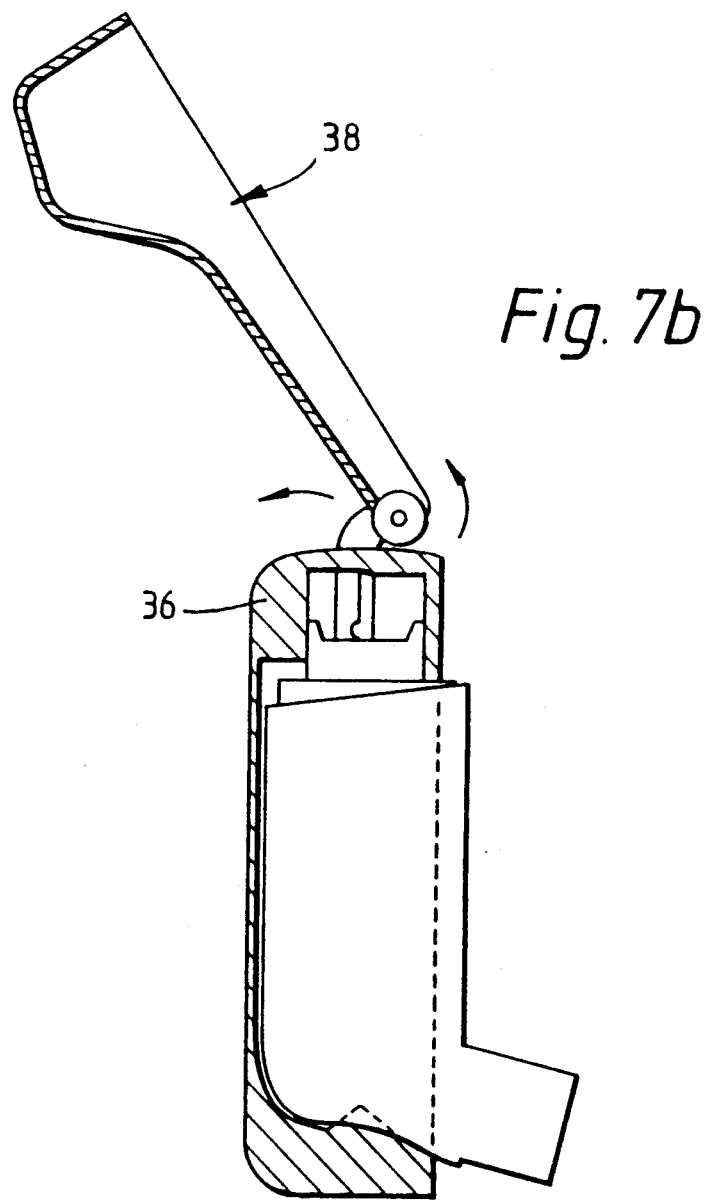

FIGS. 7a and 7b illustrate an alternative form of protective casing comprising a body portion (36) and a movable cover (38) which is pivoted from a point at the top of the body portion and provides a cocking force to the inhaler as the cover (38) is opened.

Figure 8A:
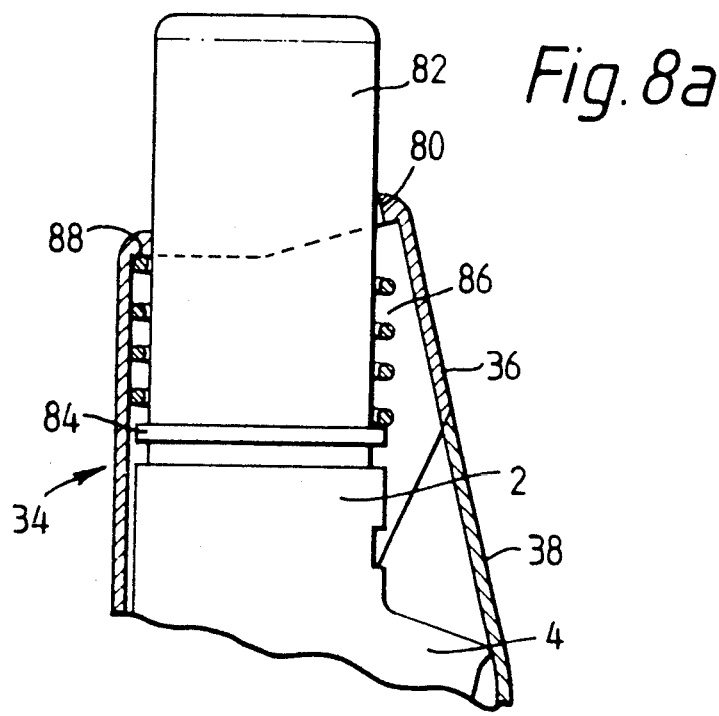
Figure 8B:
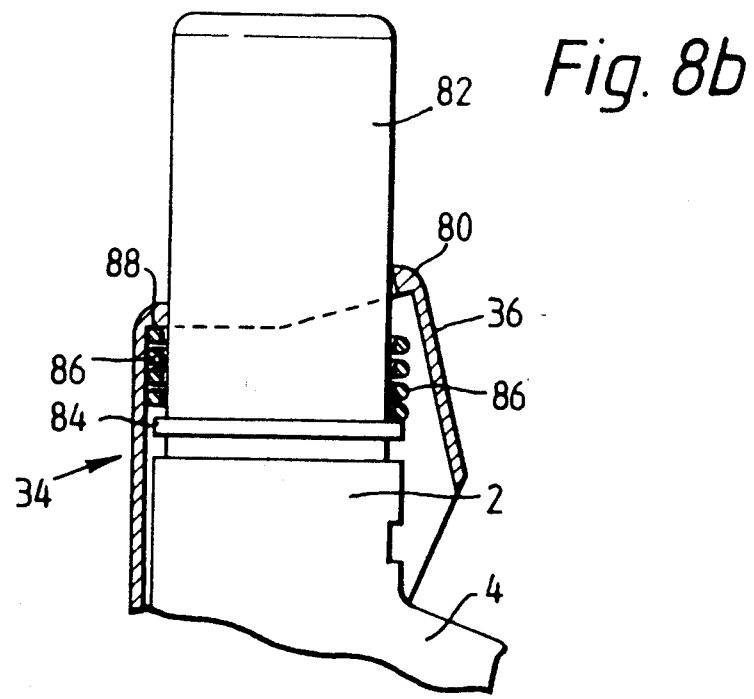

FIGS. 8a and 8b of the accompanying drawings illustrate a breath-actuated inhaler in accordance with the invention in which the protective casing (34) may be modified to accommodate aerosol vials of different length. The body portion (36) of the casing has an aperture (80) through which a shroud (82) extends which accommodates the aerosol vial (not shown). A series of shrouds (82) may be fabricated having different lengths in order to accommodate various sizes of aerosol vial.

Whilst a cocking spring may be positioned within the top of the shroud (82), in a similar manner to the cocking spring (48 shown in FIG. 4), to absorb and retain the cocking force applied when the cover (38) is opened (as described with reference to FIG. 4) a cocking spring external of the shroud (82) may be employed. The shroud (82) is provided with a flange (84) and cocking spring (86) is positioned around the shroud (82) extending between the flange (84) and a stop or the top of the protective casing (88). When the cover (38) is opened, the breath-actuated inhaler, together with the shroud (82) is lifted (FIG. 8b) compressing cocking spring (86). When the patient breathes through the mouthpiece (4), the breath-actuated mechanism is triggered moving the shroud (82) and aerosol vial downwards to fire the aerosol valve.

Figure 9A:
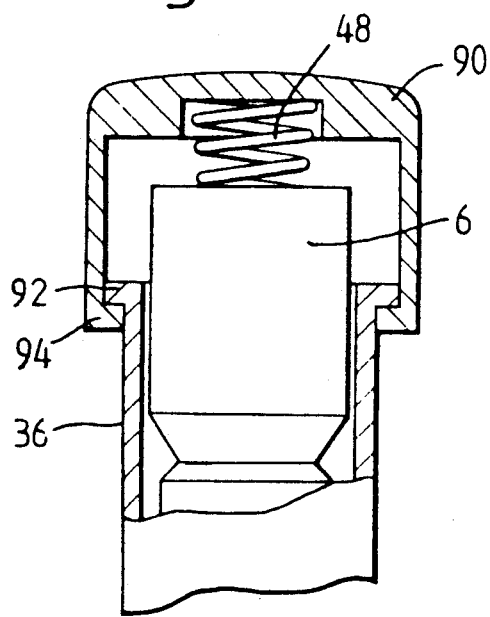
Figure 9B:
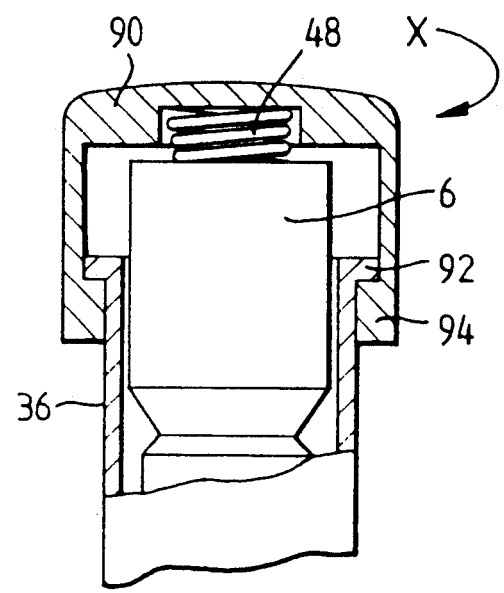

FIGS. 9a and 9b of the accompanying drawings illustrate an alternative cocking mechanism which may be incorporated into the protective casing of an inhalation device in accordance with the invention. The body portion (36) of the protective casing may comprise a separate upper portion (90) which envelopes the end of the aerosol valve (6). Cocking spring (48) is positioned within the upper portion of the casing (90) to act against the base of the aerosol vial (6). The upper portion (90) is retained on the body portion (36) of the protective casing by complimentary flanges (92 and 94) which constitute a thread segment such that rotation of the upper portion (90) in the direction of the arrow X (FIG. 9b) causes the upper portion (90) to move down the body portion (36) thereby compressing cocking spring (48) and applying the necessary cocking force for the breath-actuated mechanism.

Figure 10A:
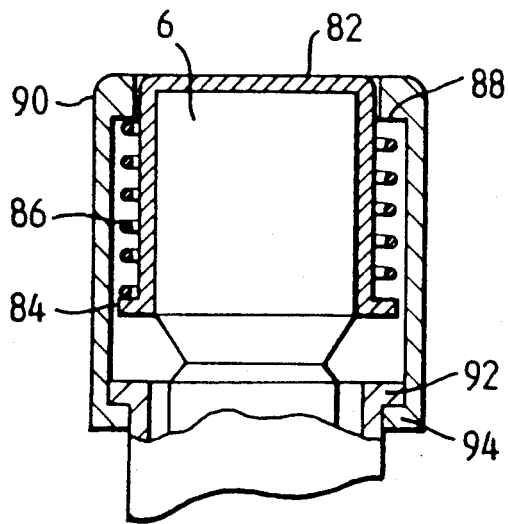
Figure 10B:
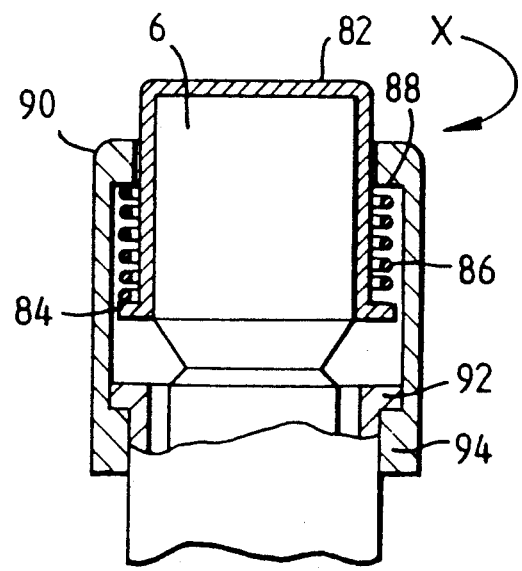

FIGS. 10a and 10b illustrate an inhalation device in accordance with the invention which incorporates the features of FIGS. 8 and 9. The top of the protective casing comprises an upper portion (90) through which extends a shroud (82) whose length is selected to accommodate the particular size of aerosol vial (6). Cocking spring (86) extends between flange (84) on the shroud and a stop or top (88) of the upper portion (90) and is compressed by downward movement of the upper portion (90) upon rotation in the direction of the arrow X. When the patient breathes through the mouthpiece (not shown) the breath-actuated device is triggered and the shroud (82) moves downwardly under the influence of the spring (86) thereby firing the aerosol valve.

In a further embodiment of the invention (not illustrated in the drawings) the shroud (82) shown in FIGS. 8 and 10 may be dispensed with and replaced by a circumferential flange extending around the aerosol vial, equivalent to flange (84), against which cocking spring (86) will act. The circumferential flange may be fabricated as a snap-on component around the aerosol vial e.g., in the region of the neck of the vial. This arrangement will obviate the need for fabricating a series of shrouds to accommodate the different sizes of aerosol vial, since the aerosol vial will simply extend through the top of the protective casing.

We claim:
1. An inhalation device comprising:
(i) a breath-actuated inhaler comprising: a medicament reservoir which comprises an aerosol vial containing propellant and medicament and equipped with a dispensing valve; and a housing which comprises a mouthpiece and breath-actuation means which prevents dispensing from the reservoir until a patient inhales through the mouthpiece, wherein the medicament reservoir is mounted within the housing, and (ii) a protective casing surrounding the breath-actuated inhaler, the casing comprising a body portion, a means for applying a cocking force to the breath-actuated inhaler, and a cover that is movable between a closed position and a displaced position that allows a patient access to the mouthpiece to use the breath-actuated inhaler whilst it is within the casing, the breath-actuated inhaler being removable from the protective casing and operable outside the casing, wherein the means for applying the cocking force comprises: an upper portion of the protective casing which is mounted on the remainder of the body portion by a screw thread arrangement, whereby rotation of the upper portion causes movement thereof along the body portion; and a spring means to actually cock the breath-actuated inhaler.

2. An inhalation device according to claim 1, wherein the breath-actuated inhaler additionally comprises means for providing an indication of the contents dispensed and/or remaining in the aerosol vial.

3. An inhalation device comprising:
(i) a breath-actuated inhaler comprising: a medicament reservoir which comprises an aerosol vial containing propellant and medicament and equipped with a dispensing valve; means to switch the inhaler from the breath-actuated mode to a press-and-breathe mode; and a housing which comprises a mouthpiece and breath-actuation means which prevents dispensing from the reservoir until a patient inhales through the mouthpiece, wherein the medicament reservoir is mounted within the housing; and (ii) a protective casing surrounding the breath-actuated inhaler, the casing comprising a body portion and a cover that is movable between a closed position and a displaced position that allows a patient access to the mouthpiece to use the breath-actuated inhaler whilst it is within the casing, the breath-actuated inhaler being removable from the protective casing and operable outside the casing.

4. An inhalation device according to claim 3, constructed and arranged such that the inhaler is converted to and maintained in a breath-actuated inhaler upon insertion into the protective casing.

5. An inhalation device comprising:
(i) a breath-actuated inhaler comprising: a medicament reservoir which comprises an aerosol vial containing propellant and medicament and equipped with a dispensing valve, a housing which comprises a mouthpiece and breath-actuation means which prevents dispensing from the reservoir until a patient inhales through the mouthpiece, wherein the medicament reservoir is mounted within the housing, and (ii) a protective casing surrounding the breath-actuated inhaler, the casing comprising a body portion and a cover that is movable between a closed position and a displaced position that allows a patient access to the mouthpiece to use the breath-actuated inhaler whilst it is within the casing, the breath-actuated inhaler being removable from the protective casing and operable outside the casing, wherein the protective casing comprises a shroud surrounding the aerosol vial, the shroud being movable within the remainder of the protective casing and spring biased to urge the aerosol vial towards a firing position.

* * * * *